US00PP20228P3

(12) United States Plant Patent
Laviana

(10) Patent No.: US PP20,228 P3
(45) Date of Patent: Aug. 18, 2009

(54) ***CAREX* PLANT NAMED 'ICE BALLET'**

(50) Latin Name: *Carex morrowii*
Varietal Denomination: Ice Ballet

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 112 days.

(21) Appl. No.: 11/975,108

(22) Filed: Oct. 17, 2007

(65) Prior Publication Data

US 2009/0106871 P1 Apr. 23, 2009

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent L Bell
(74) *Attorney, Agent, or Firm*—Penny J. Aguirre

(57) ABSTRACT

A new cultivar of *Carex morrowii,* 'Ice Ballet', characterized by its variegated foliage with creamy white margins and green centers with wider margins than is typical for other variegated cultivars of *Carex morrowii,* a clumping forming but slowly spreading habit with suitable use as a groundcover, a vigorous growth rate, and hardiness in at least U.S.D.A. Zones 4 to 9.

2 Drawing Sheets

Botanical classification: *Carex morrowii.*
Varietal denomination: 'Ice Ballet'.

BACKGROUND OF THE INVENTION

The present invention relates to a new and distinct cultivar of *Carex morrowii* and will be referred to hereafter by its cultivar name, 'Ice Ballet'. 'Ice Ballet' is a new cultivar of perennial ornamental grass grown for landscape use.

The new cultivar, 'Ice Ballet' arose as a naturally occurring chimeral mutation of *Carex morrowii* 'Ice Dance' (not patented). The inventor discovered 'Ice Ballet' in August of 2005 in his nursery in Kensington, Conn.

Asexual reproduction of the new cultivar was first accomplished by rhizome division in Kennsington, Conn. in November of 2005 by the inventor. The characteristics of this cultivar have been determined to be stable and are reproduced true to type in successive generations.

SUMMARY OF THE INVENTION

The following traits have been repeatedly observed and represent the characteristics of the new cultivar. The new *Carex* has not been observed under all possible environmental conditions. The phenotype may vary somewhat with variations in temperature, day-length, light intensity, soil types, and water and fertility levels without, however, any variance in genotype. The general observations, and descriptions that follow describe plants that were grown outdoors in a test plot in Kensington, Conn. for a period of two years. These attributes in combination distinguish 'Ice Ballet' from all other selections of *Carex* known to the inventor.

1. The foliage of 'Ice Ballet' is variegated with leaves that exhibit green centers and creamy white margins. The margins comprise about one third to one half of the leaf area, which is wider than the margins of other cultivars of *Carex morrowii.*

2. 'Ice Ballet' exhibits a plant habit that is slowly spreading by rhizomes and forming compact clumps as it spreads.
3. 'Ice Ballet' is readily propagated by rhizome division and tissue culture and has a vigorous growth habit.
4. 'Ice Ballet' is hardy at least in U.S.D.A. Zones 4 to 9.

'Ice Ballet' is similar to its parent plant, 'Ice Dance', in having variegated leaves with creamy white margins, however the margins of 'Ice Ballet' are 2 to 3 times wider. 'Ice Ballet' can be compared to other variegated forms of *Carex morrowii* known to the inventor; *Carex morrowii* 'Variegata' (not patented) differs in having inconsistent or indistinct, narrow white margins, *Carex morrowii* 'Gilt' (not patented) differs in having narrower creamy white margins and *Carex morrowii* 'Goldband' (not patented) differs in having narrow gold margins.

BRIEF DESCRIPTION OF THE DRAWING

The accompanying colored photographs illustrate the new variety.

The photograph on FIG. 1 provides a close-up of the foliage of a one year-old plant of 'Ice Ballet' as grown in a one gallon container outdoors in Kensington, Conn.

Figure 1:
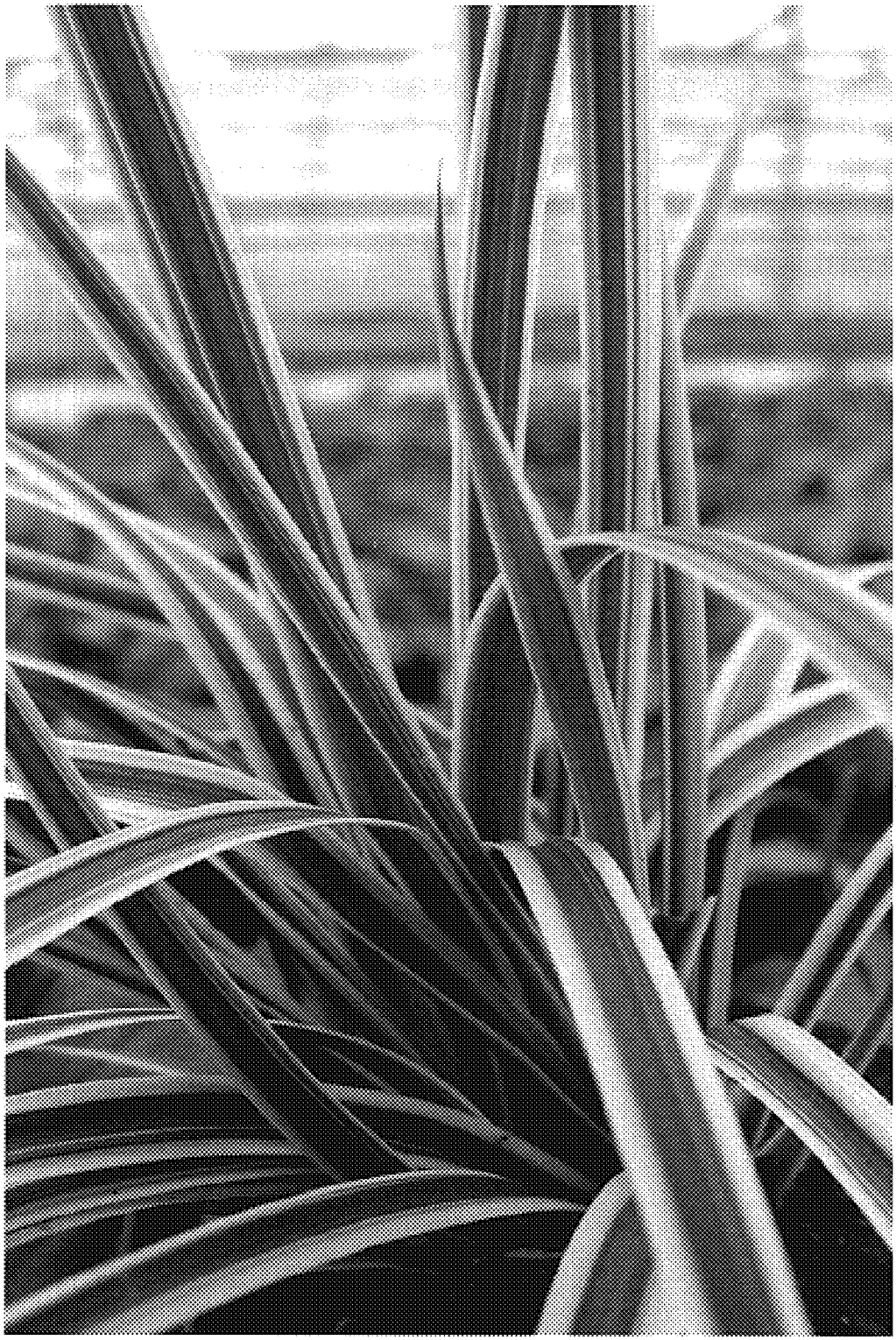
Figure 2:
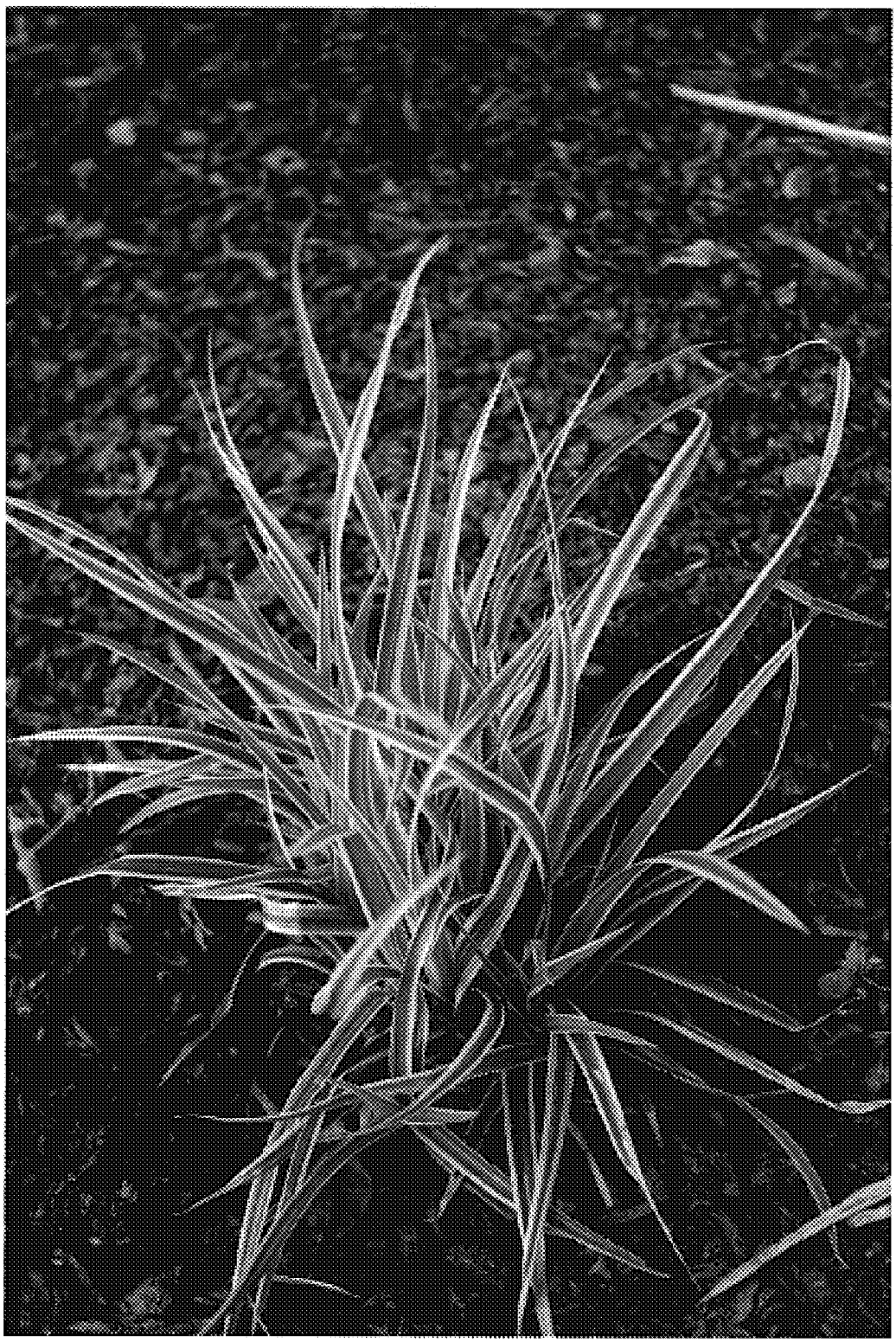

The photograph on FIG. 2 provides an overall the leaf variegation pattern and the plant habit of a two year-old plant of 'Ice Ballet' as grown in a trial bed in New Hope, Minn.

The colors in the photographs are as close as possible with the photographic and printing technology utilized and the color values cited in the detailed botanical description accurately describe the colors of the new *Carex.*

DETAILED BOTANICAL DESCRIPTION

The general observations and descriptions describe plants of 'Ice Ballet' as grown outdoors in trial beds in Kensington, Conn. and New Hope, Minn. for two growing seasons. The color determinations are in accordance with the 2001 R.H.S. Colour Chart of The Royal Horticultural Society, London, England, except where general color terms of ordinary dictionary significance are used.

General description:

*Plant habit.*—Evergreen at least to U.S.D.A. Zone 5, clump-forming and slowly spreading via rhizomes.

*Height and spread.*—Reaches about 38 cm in height and slowly spreads as a groundcover; a 3-rhizome division spreads to about 14 cm at the base and 68 cm to the edges of the foliage in two growing seasons.

*Hardiness.*—U.S.D.A. Zones 4 to 9 at a minimum, may be cold hardy to Zone 3.

*Culture.*—Grows best in part shade in fertile, well-drained soils with adequate moisture, tolerant to full shade in warmer climates and full sun in cooler climates.

*Diseases and pests.*—Typically unaffected by disease and pests.

*Root description.*—Short, stout rhizomes with fibrous roots.

*Propagation.*—Rhizome division.

*Growth rate.*—Vigorous.

*Branching.*—Stemless, shoots arise from rhizomes.

Foliage description:

*Leaf shape.*—Linear.

*Leaf division.*—Simple.

*Leaf base.*—Sheathed to rhizome.

*Leaf apex.*—Attenuate.

*Leaf aspect.*—Leaves initially emerge upright, then cascade at an average of a 45° angle.

*Leaf venation.*—Parallel, the midrib is raised on the lower surface, not prominent or conspicuous, color matches leaf color.

*Leaf margins.*—Entire, scaberulose towards apex.

*Leaf persistence.*—Persistent; evergreen under conditions tested.

*Leaf attachment.*—Sheathed.

*Leaf size.*—Matures to an average of 37 cm in length and 1 cm in width.

*Leaf number.*—Average of 15 leaves per rhizome and about 200 per plant with a base width of 14 cm in mid October.

*Leaf arrangement.*—Equitant (overlapping), emerge from center, sheathed to base.

*Leaf surface.*—Glabrous on upper and lower surface.

*Leaf variegation pattern.*—Green centers and creamy white margins with margins comprising from one third to one half of the leaf area.

*Leaf color.*—Emerging leaf color upper surface; centers 144A with margins 150C to 1D, emerging leaf color lower surface: centers 144B with margins 1D to 150C, mature leaf color upper surface: 137 A to 137B with margins 155A to 160C, mature leaf color lower surface; centers 137B with margins 155A to 160C.

Flower and seed description: Flowering has not been observed under the conditions tested.

It is claimed:

1. A new and distinct cultivar of *Carex* plant named 'Ice Ballet' as herein illustrated and described.

* * * * *